US008724880B2

United States Patent

(12) United States Patent
Shiki et al.

(10) Patent No.: US 8,724,880 B2
(45) Date of Patent: May 13, 2014

(54) ULTRASONIC DIAGNOSTIC APPARATUS AND MEDICAL IMAGE PROCESSING APPARATUS

(75) Inventors: Eiichi Shiki, Otawara (JP); Yoshihito Abe, Utsunomiya (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 64 days.

(21) Appl. No.: 13/604,324

(22) Filed: Sep. 5, 2012

(65) Prior Publication Data

US 2013/0004047 A1 Jan. 3, 2013

Related U.S. Application Data

(63) Continuation of application No. PCT/JP2012/066615, filed on Jun. 28, 2012.

(30) Foreign Application Priority Data

Jun. 29, 2011 (JP) ................................ 2011-144602

(51) Int. Cl.
*G06K 9/00* (2006.01)

(52) U.S. Cl.
USPC .......................................... 382/131; 600/437

(58) Field of Classification Search
None
See application file for complete search history.

(56) References Cited

U.S. PATENT DOCUMENTS

| | | | | |
|---|---|---|---|---|
| 8,103,066 | B2 * | 1/2012 | Kim et al. | 382/128 |
| 2002/0094115 | A1 | 7/2002 | Ogawa | |
| 2006/0058674 | A1 * | 3/2006 | Olstad | 600/450 |
| 2009/0076387 | A1 | 3/2009 | Simopoulos | |
| 2010/0049046 | A1 * | 2/2010 | Peiffer et al. | 600/443 |
| 2012/0157843 | A1 * | 6/2012 | Lavin et al. | 600/443 |

FOREIGN PATENT DOCUMENTS

| | | | |
|---|---|---|---|
| JP | 06-114060 | A | 4/1994 |
| JP | 2002-209888 | A | 7/2002 |
| JP | 2002-209889 | A | 7/2002 |
| JP | 2003-339705 | A | 12/2003 |
| JP | 2005-103129 | A | 4/2005 |
| JP | 2007-313294 | A | 12/2007 |
| JP | 2009-66420 | A | 4/2009 |
| JP | 2009-225917 | A | 10/2009 |
| JP | 2010-068987 | A | 4/2010 |

OTHER PUBLICATIONS

International Search Report dated Jul. 24, 2012 for corresponding International Application No. PCT/JP2012/066615.

* cited by examiner

*Primary Examiner* — Shefali Goradia

(74) *Attorney, Agent, or Firm* — Yoshida & Associates, LLC

(57) ABSTRACT

According to one embodiment, a gain adjustment unit executes gain adjustment for 3D B-mode data using gain adjustment values respectively decided for the depth on each scanning line, azimuth direction and elevation direction in a scanned region. A threshold decision unit decides a threshold used for discriminating lumen and non-lumen regions in the scanned region using the gain-adjustment-executed 3D B-mode data. A threshold processing unit executes threshold processing to discriminate data concerning the non-lumen region from the gain-adjustment-executed 3D B-mode data, using the threshold. An image generation unit generates an ultrasonic image concerning the lumen region based on the threshold-processing-executed 3D B-mode data.

11 Claims, 13 Drawing Sheets

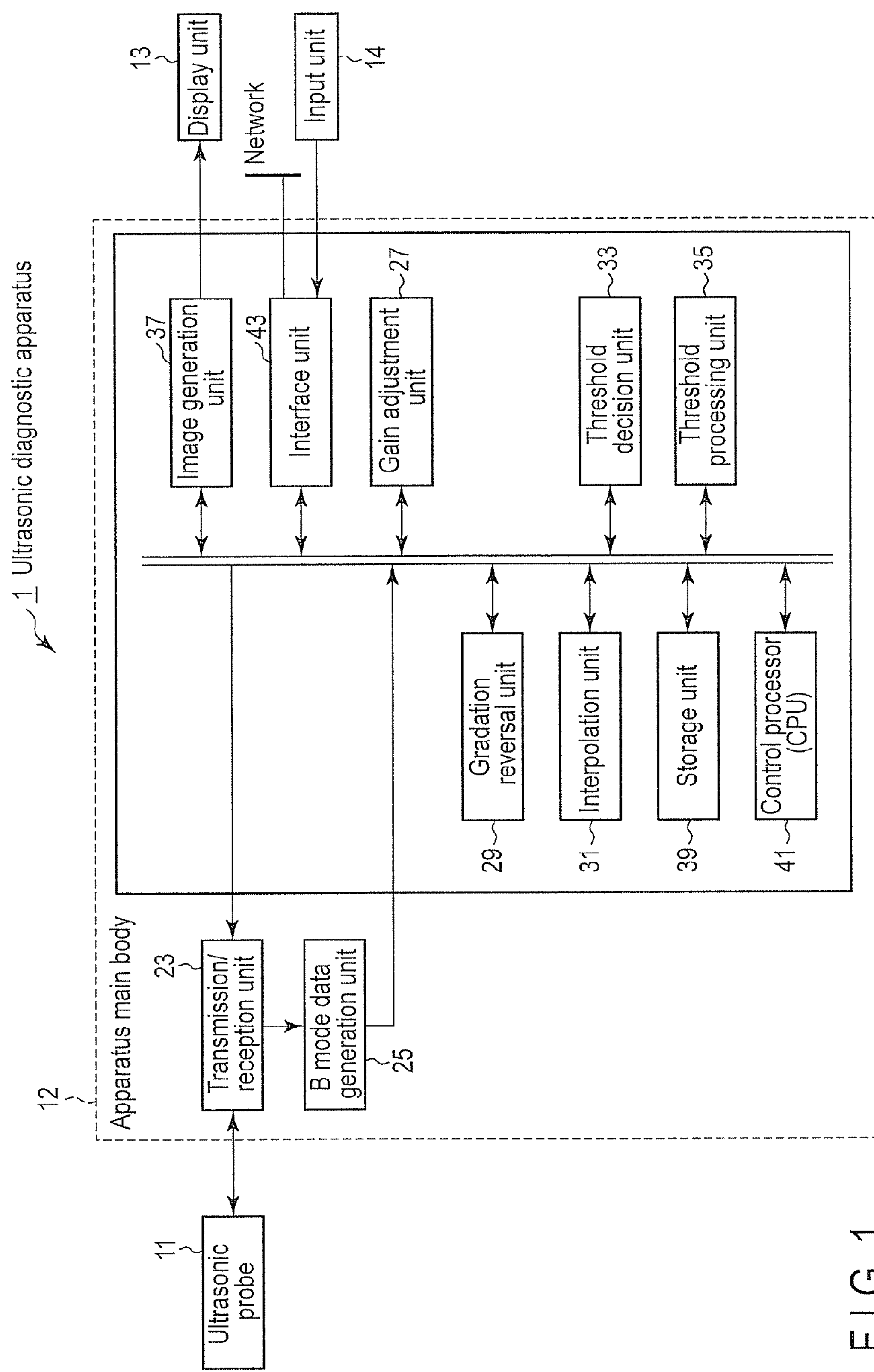
F I G. 1

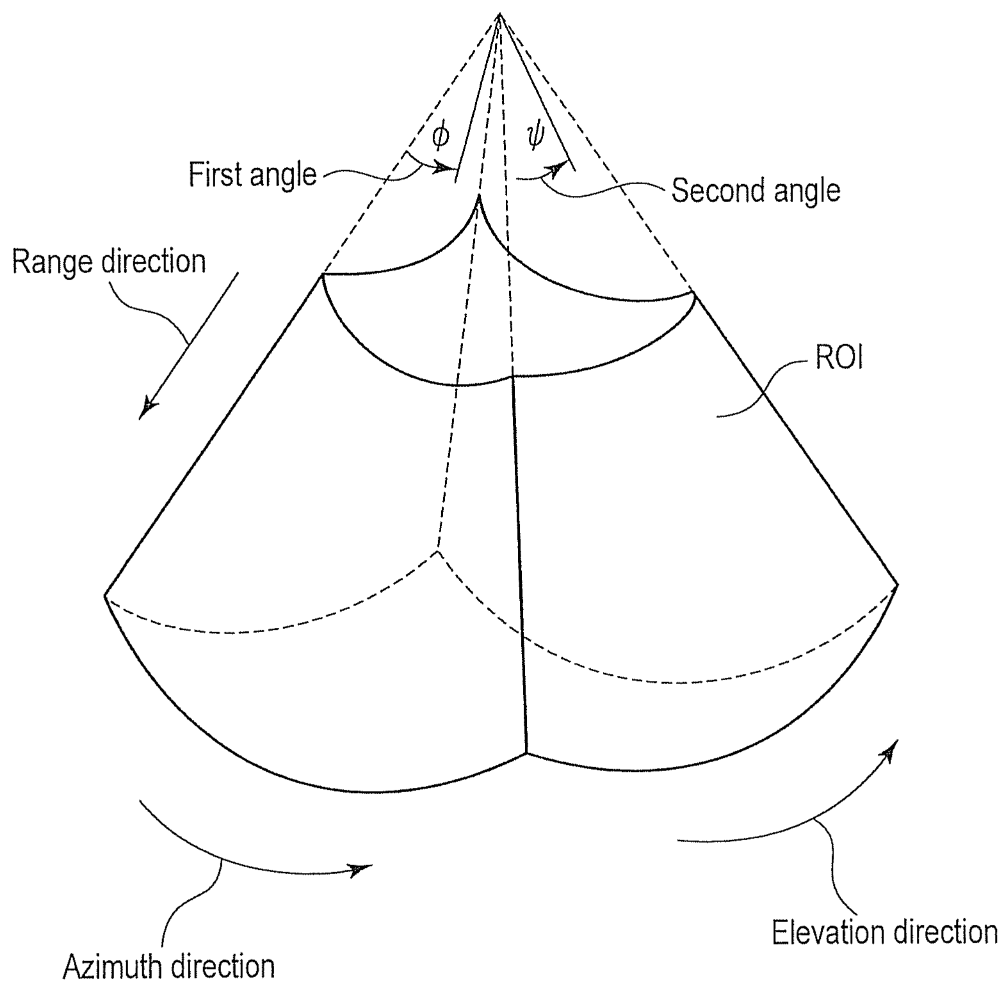
F I G. 2

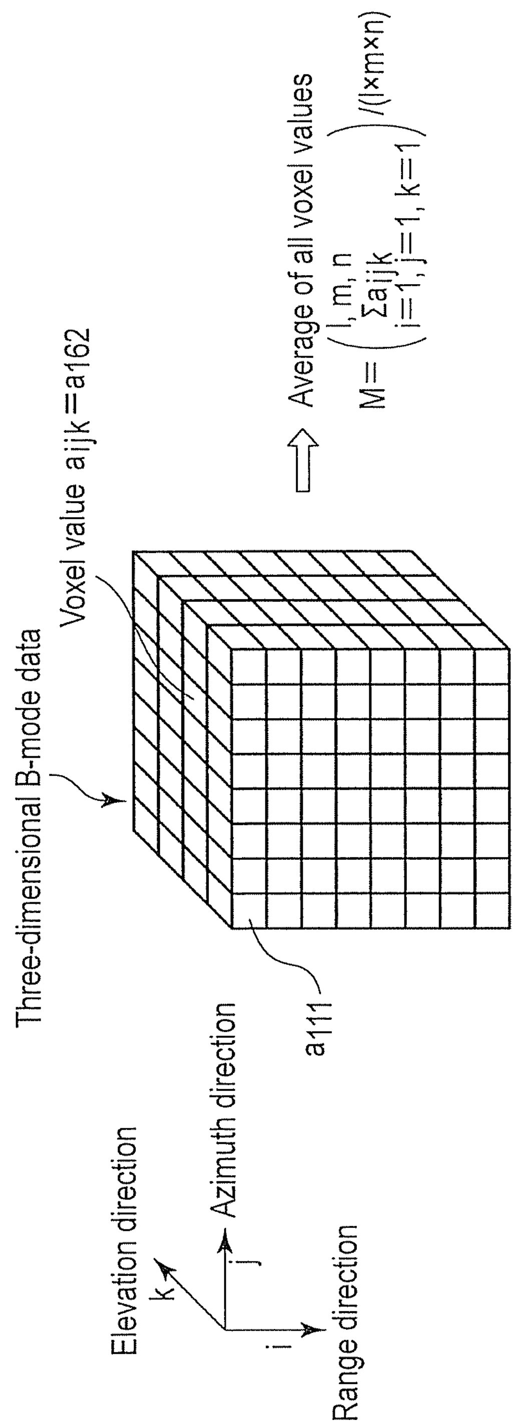
F I G. 3

Perspective projection method

View volume and line of sight

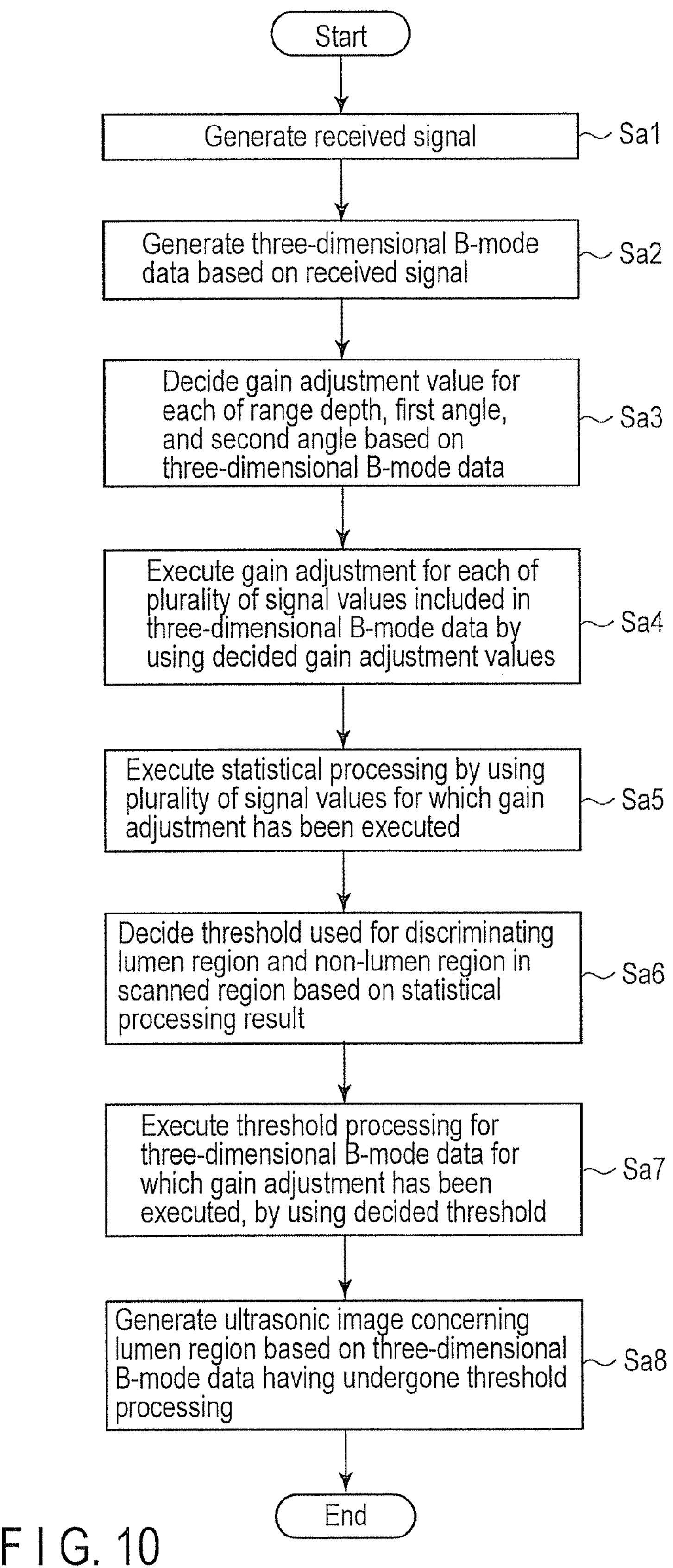
F I G. 10

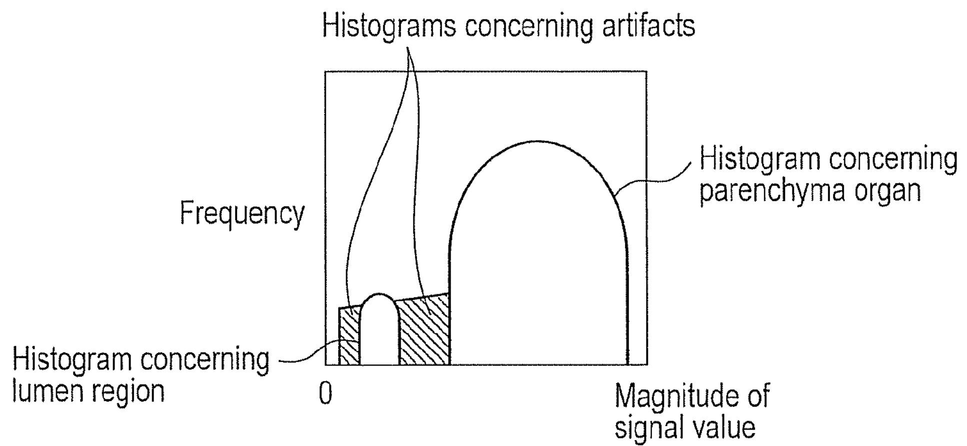
F I G.11
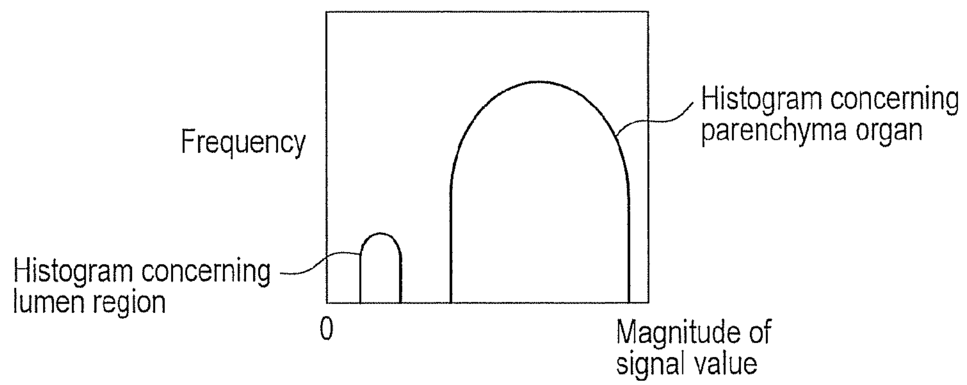
F I G.12
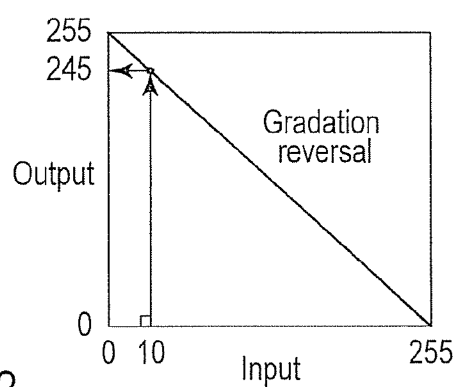
F I G.13

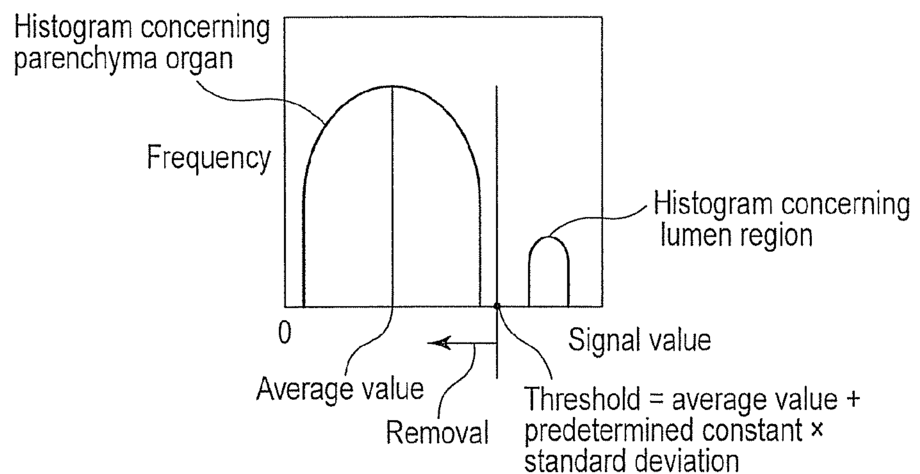
F I G. 14
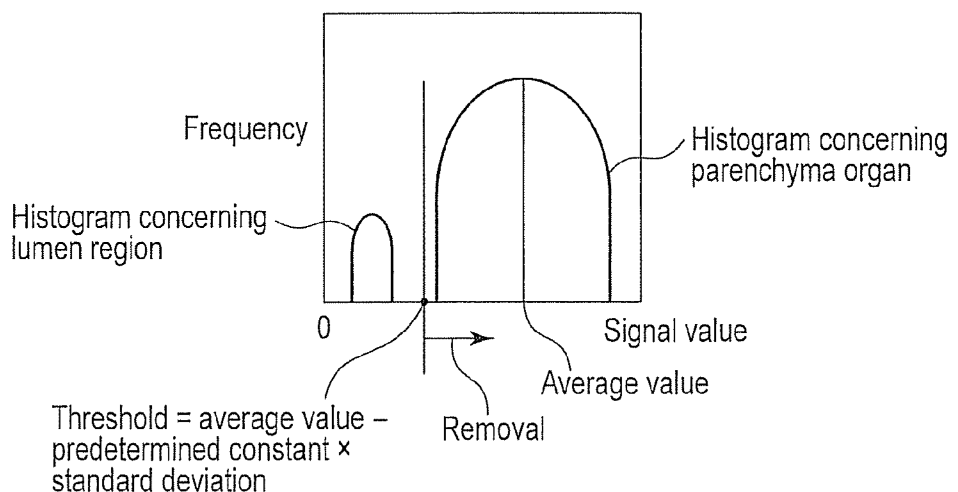
F I G. 15

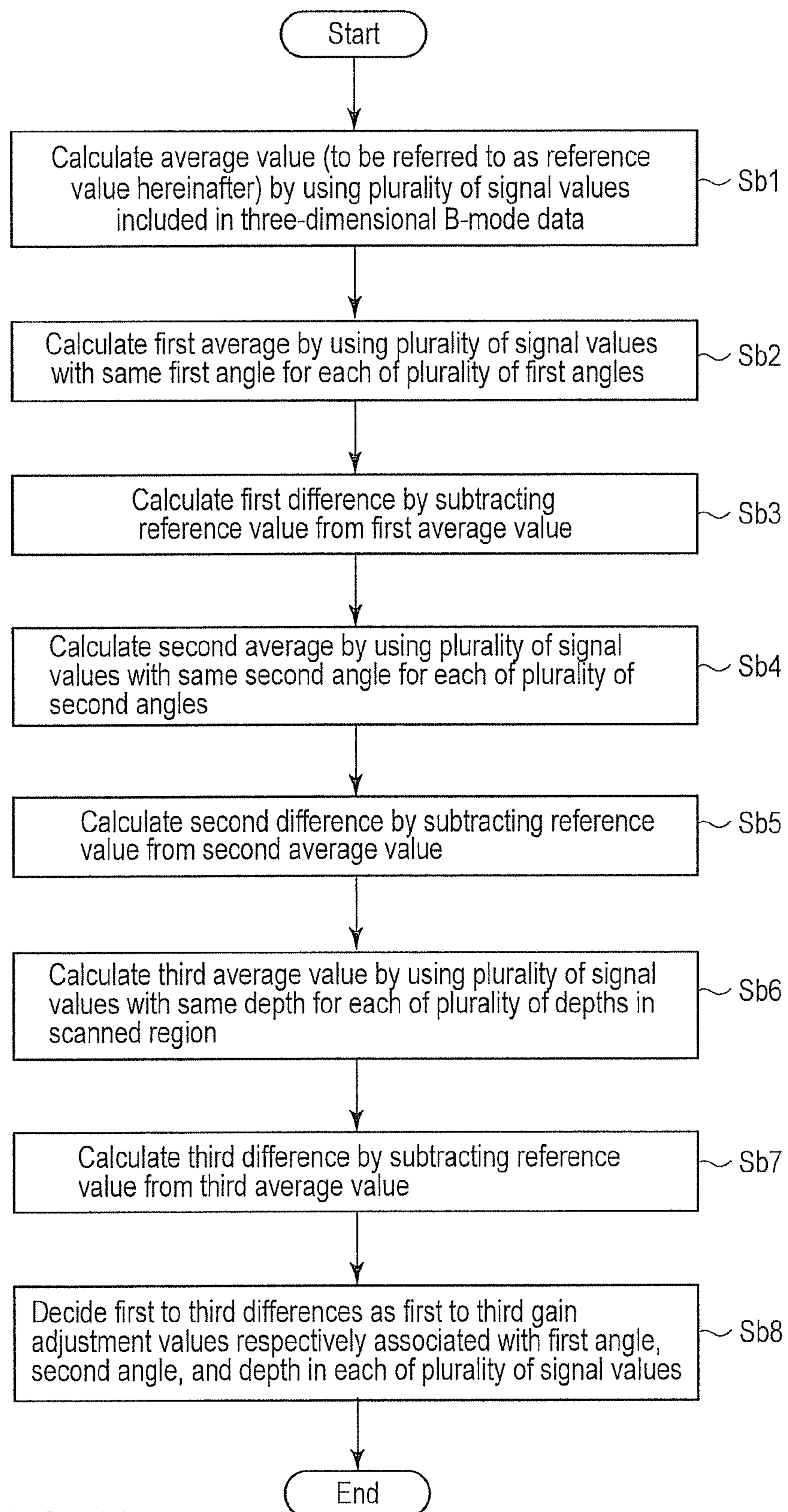
F I G. 16

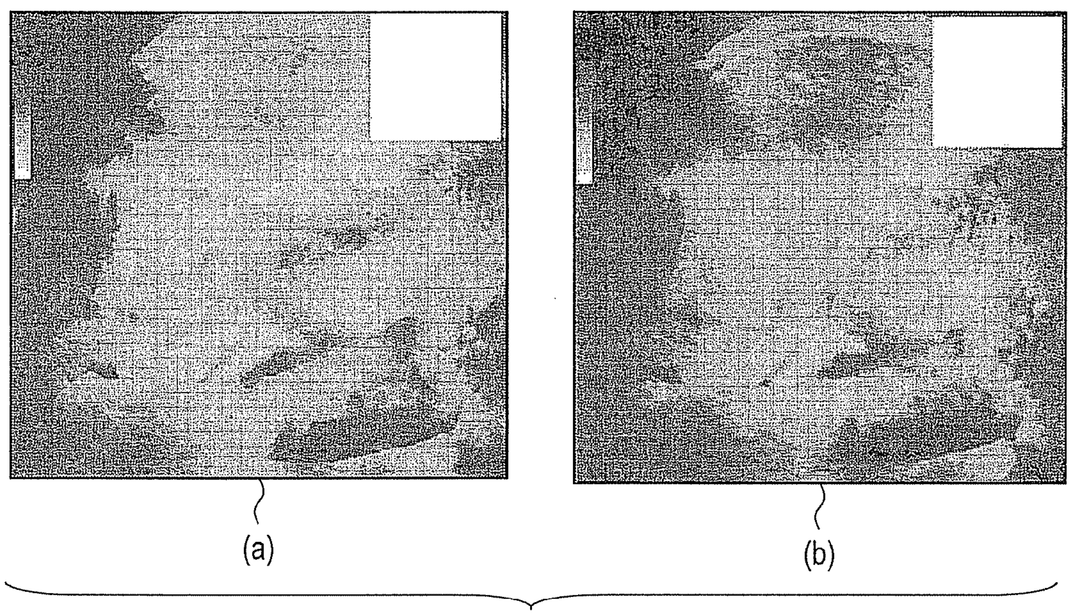
F I G. 18

ULTRASONIC DIAGNOSTIC APPARATUS AND MEDICAL IMAGE PROCESSING APPARATUS

CROSS-REFERENCE TO RELATED APPLICATIONS

This application is a Continuation Application of PCT Application No. PCT/JP2012/066615, filed Jun. 28, 2012 and based upon and claiming the benefit of priority from Japanese Patent Application No. 2011-144602, filed Jun. 29, 2011, the entire contents of all of which are incorporated herein by reference.

FIELD

Embodiments described herein relate generally to an ultrasonic diagnostic and a medical image processing apparatus.

BACKGROUND

Recently, an ultrasonic diagnostic apparatus has been put to practical use, which acquires echo signals from an object by three-dimensionally scanning the object. This ultrasonic diagnostic apparatus can generate and display a three-dimensional image (e.g., a rendering image) by generating three-dimensional B-mode data based on an echo signal.

There is available an imaging method (to be referred as a cavity imaging method hereinafter) which three-dimensionally displays a lumen region (e.g., a blood vessel or biliary duct) in a scanned region with high luminance. An image generated by the cavity imaging method will be called a cavity image hereinafter. A cavity image is generated by reversing the gradations of three-dimensional B-mode data and then generating a three-dimensional image (e.g., a rendering image).

Gradation reversal will be described below. Assume that the gradation values of B-mode data range from 0 to 255, and the gradation value of given B-mode data is 10. In this case, reversing the gradation is to change the gradation value of the B-mode data to 255−10=245. A gradation value corresponds to a luminance value. If, therefore, the gradation value of the B-mode data is a low gradation like 10, it corresponds to a low luminance. If the gradation value of the B-mode data is a high gradation like 245, it corresponds to a high luminance.

The cavity imaging method is designed to reverse the gradations of a plurality of signal values or a plurality of pixel values of three-dimensional B-mode data. Performing gradation reversal will change the gradation of virtual data concerning a non-lumen region (e.g., a parenchyma organ or the like in the object) with a high gradation (high luminance) to a low gradation (low luminance). This operation also changes the gradations of lumen data concerning the lumen region with low gradations (low luminances) or in a transparent state to high gradations (high luminances). With this operation, the lumen region is displayed. Note that in this state, since virtual data lower in gradation than the lumen region exist outside the high-gradation lumen region, non-lumen region may be displayed so as to surround the lumen region, as shown in (a) in FIG. 17. In this case, it is difficult to recognize the lumen region. At this time, setting a threshold and removing virtual data lower in gradation than the threshold can display only the high-gradation lumen region. For the sake of printing, (a) in FIG. 17 shows a black/white reversed image. The same applies to the images shown in (b) in FIG. 17, (c) in FIG. 17, (a) in FIG. 18, and (b) in FIG. 18.

In practice, however, since echo signals are attenuated due to insufficient contact between an object surface and the ultrasonic probe or the attenuation of the intensity of ultrasonic waves at deep portions in a scanned region, mainly the virtual data at side and deep portions in the scanned region have low gradations. In a gradation-reversed cavity image, therefore, the virtual data at side and deep portions have high gradations like the lumen region. For this reason, as indicated by (b) in FIG. 17, threshold processing cannot remove virtual data. The virtual data which are not removed by threshold processing become artifacts in the cavity image. These artifacts decrease the detection performance and diagnostic performance concerning the lumen region by the operator. At this time, increasing the threshold to eliminate artifacts will simultaneously make the lumen region disappear as indicated by (c) in FIG. 17. It is therefore difficult to avoid the influences of artifacts by threshold processing.

The above method of reducing artifacts is a method using a volume removal function. In this method, first of all, the apparatus sets, on a displayed cavity image, the region input by the operator via a trackball. The apparatus then removes a volume image concerning the set region in response to switching operation on the panel of an input unit. The apparatus repeats the above procedure several to ten several times while rotating a cavity image. The above procedure eliminates artifacts. Since this method makes the operator perform input operation to set a region from which artifacts are removed, some artifacts remain unremoved. For this reason, the detection performance and diagnostic performance concerning the lumen region decrease. In addition, since it takes labor and time to set the above region, the method is difficult to execute at the stage of examination and hence is not practical.

In addition, although the initial value of the threshold is set in advance to a value regarded as proper, the optimal threshold generally differs depending on the object and diagnostic region. It is therefore difficult to always set the threshold to the optimal value in an initial state. For this reason, as indicated by (a) in FIG. 18, in an initial state, the apparatus generally displays an image in which many non-lumen regions such as parenchyma organs remain or an inappropriate image in which many parts of the lumen region are lost. At this time, it is necessary to change the threshold to a proper value by making the operator operate a knob or slider on the panel. In addition, when the operator changes the gain value by using a B-mode gain knob to adjust the luminance of a B-mode image, the apparatus also changes the gradation values of the volume image, as indicated by (b) in FIG. 18. This makes it necessary to re-set the threshold. That is, it is necessary to change the threshold setting every time the diagnostic region and gain value concerning a B-mode image are changed. This leads to poor operability and hence to poor examination efficiency.

BRIEF DESCRIPTION OF THE DRAWINGS

FIG. 1 is a block diagram showing the arrangement of an ultrasonic diagnostic apparatus according to this embodiment.

FIG. 2 is a view showing an example of an ROI in a scanned region according to this embodiment.

FIG. 3 is a view showing an example of a predetermined reference value calculated based on three-dimensional B-mode data according to this embodiment.

FIG. 10 is a flowchart showing a procedure for the processing of generating an ultrasonic image concerning the lumen region according to this embodiment.

FIG. 11 is a view showing an example of histograms concerning a plurality of signal values included in three-dimensional B-mode data before gain adjustment according to this embodiment.

FIG. 12 is a view showing an example of histograms concerning a plurality of signal values included in the three-dimensional B-mode data after gain adjustment.

FIG. 13 is a view showing an example of a graph concerning gradation reversal according to this embodiment.

FIG. 14 is a view showing histograms of a plurality of signal values included in three-dimensional B-mode data having undergone gain adjustment and gradation reversal, together with a decided threshold, according to this embodiment.

FIG. 15 is a view showing histograms of a plurality of signal values included in three-dimensional B-mode data after gain adjustment, together with a threshold, when histogram signals concerning a parenchyma organ are removed before gradation reversal, according to this embodiment.

FIG. 16 is a flowchart showing a procedure for the processing of deciding a gain adjustment value according to step Sa3 in FIG. 10 according to this embodiment.

FIG. 18 shows an example of a conventional cavity image.

DETAILED DESCRIPTION

Figure 4:
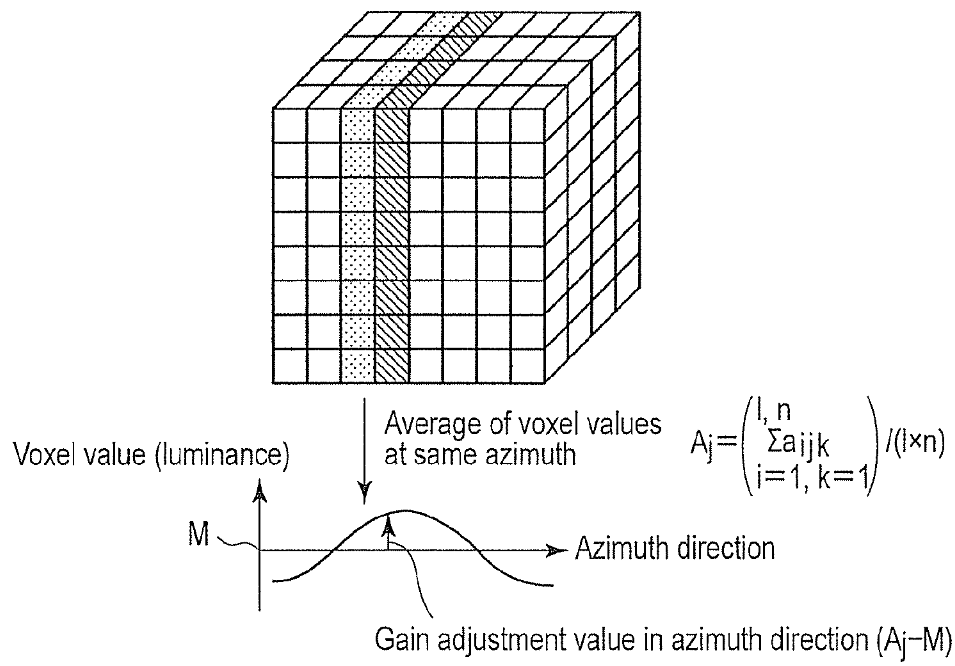
FIG. 4 is a view showing an example of a gain adjustment value in the azimuth direction according to this embodiment.

In general, according to one embodiment, in an ultrasonic diagnostic apparatus includes an ultrasonic probe, a transmission/reception unit, a B-mode data generation unit, a gain adjustment unit, a threshold decision unit, a threshold processing unit, an image generation unit.

The ultrasonic probe is configured to include a plurality of ultrasonic transducers.

The transmission/reception unit is configured to supply a driving signal to each of the ultrasonic transducers and generate a received signal corresponding to a scanned region based on each reception echo signal generated by each of the ultrasonic transducers.

The B-mode data generation unit is configured to generate three-dimensional B-mode data based on the received signal.

The gain adjustment unit is configured to execute gain adjustment for the three-dimensional B-mode data by using gain adjustment values respectively decided for a depth on each scanning line, an azimuth direction and an elevation direction in the scanned region.

The threshold decision unit is configured to decide a threshold used for discriminating a lumen region and a non-lumen region in the scanned region by using the three-dimensional B-mode data for which the gain adjustment has been executed.

The threshold processing unit configured to execute threshold processing to discriminate data concerning the non-lumen region from the three-dimensional B-mode data for which the gain adjustment has been executed, by using the decided threshold.

The image generation unit is configured to generate an ultrasonic image concerning the lumen region based on the three-dimensional B-mode data for which the threshold processing has been executed.

An ultrasonic diagnostic apparatus according to this embodiment will be described below with reference to the accompanying drawings. Note that the same reference numerals in the following description denote constituent elements having almost the same functions and arrangements, and a repetitive description will be made only when required.

FIG. 1 is a block diagram showing the arrangement of an ultrasonic diagnostic apparatus 1 according to this embodiment. As shown in FIG. 1, the ultrasonic diagnostic apparatus 1 includes an ultrasonic probe 11, an apparatus main body 12, a display unit 13, and an input unit 14 which is connected to the apparatus main body 12 and serves to input various kinds of instructions, commands, and information from the operator to the apparatus main body 12. In addition, a biological signal measurement unit (not shown) typified by an electrocardiograph, phonocardiograph, sphygmograph, or respiration sensor and a network may be connected to the ultrasonic diagnostic apparatus 1 via an interface unit 43. The following is a case (single sweep) in which the apparatus scans one volume as a scanned region, stops scanning, and displays an image of one volume concerning the scan. However, this embodiment is not limited to the single sweep mode. That is, the embodiment can also be applied to a case in which the apparatus scans in real time and a case in which the operator performs freeze operation via the input unit 14 during scanning in real time.

The ultrasonic probe 11 includes piezoelectric transducers as reversible acoustic/electric conversion elements such as piezoelectric ceramic elements. A plurality of piezoelectric transducers are juxtaposed and mounted on the distal end of the ultrasonic probe 11. Assume that in the following description, one piezoelectric transducer forms one channel. Each piezoelectric transducer generates an ultrasonic wave in response to a driving signal supplied from a transmission/reception unit 23 (to be described later). Each piezoelectric transducer generates a reception echo signal in response to the reception of an ultrasonic wave (to be referred to as an echo signal hereinafter) reflected by a living tissue of an object. The ultrasonic probe 11 will be described below as a mechanical four-dimensional probe which executes three-dimensional scanning by swinging a one-dimensional array in a direction perpendicular to the array direction of a plurality of transducers. Note that the ultrasonic probe 11 is not limited to a mechanical four-dimensional probe, and it is possible to use a two-dimensional array probe.

The apparatus main body 12 includes the transmission/reception unit 23, a B-mode data generation unit 25, a gain adjustment unit 27, a gradation reversal unit 29, an interpolation unit 31, a threshold decision unit 33, a threshold processing unit 35, an image generation unit 37, a storage unit 39, a control processor (central processing unit to be referred to as a CPU hereinafter) 41, and an interface unit 43. Note that the apparatus main body 12 may include a color/Doppler processing unit (not shown) which generates color/Doppler signals.

The transmission/reception unit 23 includes a trigger generation circuit, a transmission delay circuit, a pulser circuit, a preamplifier circuit, an analog/digital (to be referred to as A/D hereinafter) converter, a reception delay circuit, and an adder (none of which are shown). The trigger generation circuit repetitively generates rate pulses for the formation of transmission ultrasonic waves at a predetermined rate frequency. The trigger generation circuit repetitively generates rate pulses at a rate frequency of, for example, 5 kHz. These rate pulses are distributed to channel counts and sent to the transmission delay circuit. The transmission delay circuit gives each rate pulse a delay time necessary to focus an ultrasonic wave into a beam and determine transmission directivity for each channel. The pulser circuit applies a voltage pulse (driving signal) to each transducer of the ultrasonic probe 11 at the timing based on this rate pulse, thereby transmitting ultrasonic beams to the object.

The apparatus receives the echo signal reflected by the living tissue of the object as a reception echo signal via the ultrasonic probe 11 for each channel. The preamplifier circuit amplifies the reception echo signal received from the object via the ultrasonic probe 11 for each channel. The A/D converter converts each amplified reception echo signal into a digital signal. The reception delay circuit gives the echo signals converted into digital signals delay times required to determine reception directivity. The adder adds a plurality of echo signals given the delay times. With this addition, the transmission/reception unit 23 generates a received signal with a reflection component from a direction corresponding to the reception directivity being enhanced. The transmission directivity and the reception directivity determine the comprehensive directivity of ultrasonic transmission/reception (which in turn determines so-called "ultrasonic scanning lines"). The transmission/reception unit 23 outputs a received signal for each depth on each scanning line in a scanned region to the B-mode data generation unit 25 (to be described later). Note that the transmission/reception unit 23 may have a parallel reception function of simultaneously receiving echo signals generated on a plurality of scanning lines by one ultrasonic transmission.

The B-mode data generation unit 25 includes an envelope detector and logarithmic converter (none of which are shown). The envelope detector performs envelope detection of the received signal output from the transmission/reception unit 23. The envelope detector outputs the envelope-detected signal to the logarithmic converter (to be described later). The logarithmic converter relatively enhances a weak signal by logarithmically converting the envelope-detected signal. The B-mode data generation unit 25 generates a signal value (B-mode data) for each depth on each scanning line based on the signal enhanced by the logarithmic converter.

The B-mode data generation unit 25 generates raw data which is B-mode data having a plurality of signal values arranged in the azimuth direction (in which the transducers are arrayed), the elevation direction (the swinging direction of the scan surface), and the depth direction (to be referred to as the range direction hereinafter) in a scanned region. Note that in this embodiment, raw data, the volume data generated by the interpolation unit 31 (to be described later), and line-of-sight data will be generically written as three-dimensional B-mode data. For the sake of simplicity, the term "three-dimensional B-mode data" will be handled as a generic term of these words or will be handled in consideration of raw data without loss of generality. Note that raw data may be data obtained by arranging a plurality of pixel values, a plurality of luminance values, or the like in the azimuth direction, elevation direction, and range direction along scanning lines. In addition, three-dimensional B-mode data may be data concerning a region of interest (to be referred to as an ROI hereinafter) in a scanned region. For the sake of simplicity, assume that three-dimensional B-mode data is data concerning an ROI. The B-mode data generation unit 25 outputs the three-dimensional B-mode data to the gain adjustment unit 27 (to be described later).

Note that the B-mode data generation unit 25 may store three-dimensional B-mode data in a memory (not shown). In addition, when storing three-dimensional B-mode data in the memory (not shown), the B-mode data generation unit 25 may execute the above arranging operation in the azimuth direction, elevation direction, and range direction.

FIG. 2 is a view showing an example of an ROI in a scanned region. The region enclosed by the solid line in FIG. 2 indicates an ROI. The first angle (ϕ) in FIG. 2 indicates an angle defining a scan range in the azimuth direction. The second angle (ϕ) in FIG. 2 indicates an angle defining a scan range in the elevation direction. Note that the first and second angles may be angles defining an ROI. Referring to FIG. 2, the center of a swing angle in the azimuth direction coincides with that in the elevation direction. However, they need not always coincide with each other. In addition, referring to FIG. 2, the one-dimensional array is of a so-called convex type having a curvature. However, this embodiment is not limited to this, and the one-dimensional array may be of a so-called linear type having an infinite radius of curvature. In this case, the scanning lines in the azimuth direction become parallel to each other, and hence the first angle cannot define a scan arrange in the azimuth direction. Assume however that the first angle will be used in correspondence with a position in the one-dimensional array transducer arrangement.

If the ultrasonic transducers are arranged in a two-dimensional array, the transducers are sometimes arranged in a linear type array also in the elevation direction. In this case as well, the second angle is used in correspondence with a position in the transducer arrangement in the elevation direction. When the apparatus performs sector scanning by using a two-dimensional array, the scheme shown in FIG. 2 can be applied except that the apparatus scans scanning lines in a sector form with the center of the swing angle being placed on a transducer. As described above, the scheme in FIG. 2 is not limited to any specific probe type or scanning method and can be applied more generally by proper interpretation.

The gain adjustment unit 27 decides a gain adjustment value, based on the three-dimensional B-mode data, for each of the depth in the range direction (to be referred to as a range depth hereinafter) on each scanning line in a scanned region, the first angle, and the second angle. The gain adjustment unit 27 executes gain adjustment for each of a plurality of signal values included in three-dimensional B-mode data by using the decided gain adjustment value. Note that the gain adjustment unit 27 may execute gain adjustment for each of a plurality of pixel values included in three-dimensional B-mode data by using the decided gain adjustment value. In addition, the gain adjustment unit 27 can use not only raw data as three-dimensional B-mode data but also the volume data or line-of-sight data generated by the interpolation unit 31 (to be described later). The gain adjustment unit 27 outputs the gain-adjusted three-dimensional B-mode data to the gradation reversal unit 29.

More specifically, the gain adjustment unit 27 calculates a predetermined reference value concerning the overall three-dimensional B-mode data based on a plurality of signal values included in the three-dimensional B-mode data. A predetermined reference value is, for example, the average value of a plurality of signal values included in three-dimensional B-mode data. Note that a predetermined reference value may be a representative value (e.g., a mode value or median value) other than the average value of a plurality of signal values or a predetermined value set in advance. The gain adjustment unit 27 calculates, for each first angle, a first representative value representing a plurality of signal values included in three-dimensional B-mode data with the same first angle. The gain adjustment unit 27 calculates, for each second angle, a second representative value representing a plurality of signal values included in the three-dimensional B-mode data with the same second angle. The gain adjustment unit 27 calculates, for each depth, a third representative value representing a plurality of signal values included in the three-dimensional B-mode data with the same range depth.

The first representative value is, for example, the average value of a plurality of signal values included in three-dimensional B-mode data with the same first angle. The second representative value is, for example, the average value of a plurality of signal values included in the three-dimensional B-mode data with the same second angle. The third representative value is, for example, the average value of a plurality of signal values included in the three-dimensional B-mode data with the same depth. Note that the first to third representative values may be mode values, median values, or the like. The gain adjustment unit 27 can also use pixel values or luminance values instead of signal values. Furthermore, the gain adjustment unit 27 may use the three-dimensional B-mode data whose gradations are reversed by the gradation reversal unit 29 (to be described later).

The gain adjustment unit 27 calculates the first gain adjustment value for each first angle by subtracting a predetermined reference value from the first representative value. The gain adjustment unit 27 calculates the second gain adjustment value for each second angle by subtracting a predetermined reference value from the second representative value. The gain adjustment unit 27 calculates the third gain adjustment value for each depth by subtracting a predetermined reference value from the third representative value. The first to third gain adjustment values will be generically referred to as gain adjustment values hereinafter. The gain adjustment unit 27 executes gain adjustment for each of a plurality of signal values defined by the first and second angles and the depths by using gain adjustment values.

Decision of gain adjustment values will be described in more detail below with reference to FIGS. 3, 4, 5, and 6.

FIG. 3 is a view showing three-dimensional B-mode data by using an orthogonal coordinate system in which the range direction, azimuth direction, and elevation direction are perpendicular to each other. Referring to FIG. 3, each of a plurality of sample points respectively corresponding to a plurality of signal values included in the three-dimensional B-mode data will be referred to as a voxel. The term "voxel" used in this case is used in a broader sense than that in raw voxel conversion, and generally indicates a sample point in a three-dimensional target region. Referring to FIG. 3, the rectangular parallelepiped representing three-dimensional B-mode data does not represent the shape of a three-dimensional scanned region (to be referred to a scan shape hereinafter) unlike FIG. 2. As shown in FIG. 2, a scan shape is, for example, a shape spreading in a sector form in the azimuth direction and the elevation direction toward a deeper position in the range direction in a convex type mechanical four-dimensional probe having a one-dimensional array arranged with a predetermined curvature.

For the sake of simplicity, each of a plurality of signal values will be described as a value in a voxel (to be referred to as a voxel value $a_{ijk}$ hereinafter). The subscript "i" of a voxel value indicates the $i^{th}$ position (corresponding to a depth) from the origin ($a_{111}$ in FIG. 3) along the range direction. The subscript "j" of the voxel value indicates the jth position (corresponding to the first angle) from the origin along the azimuth direction. The subscript "k" of the voxel value indicates the kth position (corresponding to the second angle) from the origin along the elevation direction. For example, $a_{ijk}$ in FIG. 3 corresponds to $a_{162}$. For the sake of simplicity, assume that the ranges of the subscripts "i", "j", and "k" are defined as $1 \le i \le l$, $1 \le j \le m$, and $1 \le k \le n$. That is, the total number of voxels included in the rectangular parallelepiped in FIG. 3 is $l \times m \times n$. Note that if the volume data generated by the interpolation unit 31 (to be described later) is used as three-dimensional B-mode data instead of raw data, the range direction, azimuth direction, and elevation direction in FIG. 3 respectively correspond to orthogonal three axis directions in an orthogonal coordinate system in a real space. In addition, when the line-of-sight data generated by the interpolation unit 31 (to be described later) is used as three-dimensional B-mode data, the range direction, azimuth direction, and elevation direction in FIG. 3 respectively correspond to the range (depth) direction of a line of sight and the directions of two different sides of the near plane in FIG. 8.

The gain adjustment unit 27 calculates, as a predetermined reference value, an average value M of voxel values in an overall ROI by dividing the sum of voxel values in a rectangular parallelepiped by the total number of voxels. More specifically, the gain adjustment unit 27 calculates the average value M by the following equation:

$$M = \left( \sum_{i=1,j=1,k=1}^{l,m,n} a_{ijk} \right) \Big/ (l \times m \times n)$$

FIG. 4 is a view showing an example of a gain adjustment value in the azimuth direction according to this embodiment. The gain adjustment unit 27 calculates the first representative value (the average value of the voxel values at the same azimuth) for each first angle (the azimuth direction). More specifically, the gain adjustment unit 27 calculates a first representative value $A_j$ by the following equation:

$$A_j = \left( \sum_{i=1,k=1}^{l,n} a_{ijk} \right) \Big/ (l \times n)$$

The gain adjustment unit 27 then calculates a first gain adjustment value ($A_j$−M) corresponding to each first angle by subtracting the average value M from the first representative value $A_j$ corresponding to each first angle.

Figure 5:
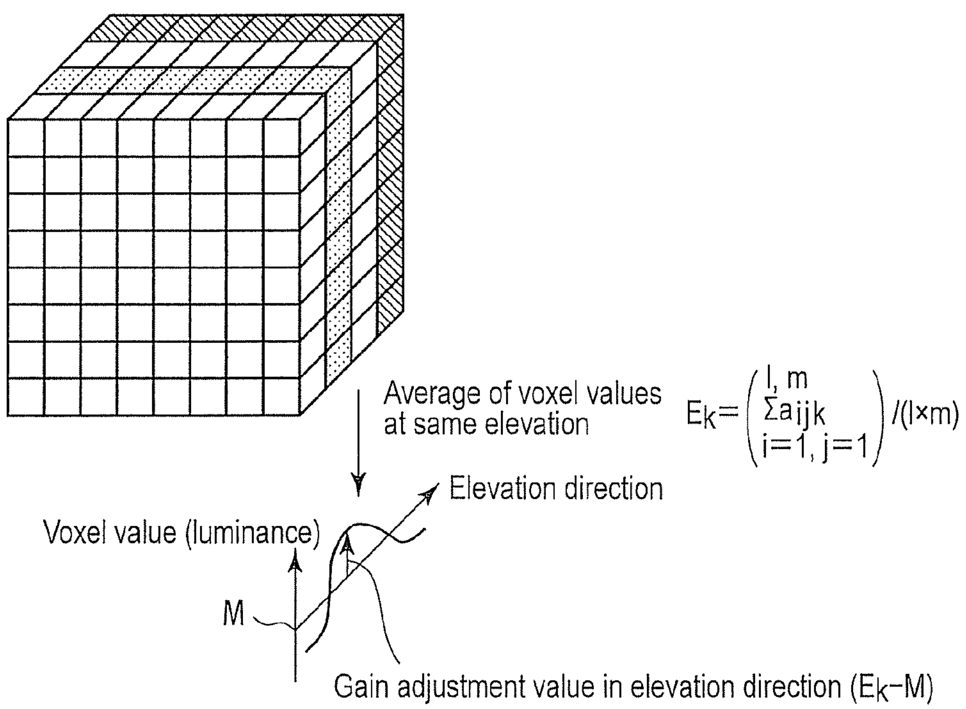
FIG. 5 is a view showing an example of a gain adjustment value in the elevation direction according to this embodiment.

FIG. 5 is a view showing an example of a gain adjustment value in the elevation direction according to this embodiment. The gain adjustment unit 27 calculates the second representative value (the average value of the voxel values at the same elevation) for each second angle (the elevation direction). More specifically, the gain adjustment unit 27 calculates a second representative value $E_k$ by the following equation:

$$E_k = \left( \sum_{i=1,j=1}^{l,m} a_{ijk} \right) \Big/ (l \times m)$$

The gain adjustment unit 27 then calculates a second gain adjustment value ($E_k$−M) corresponding to each second angle by subtracting the average value M from the second representative value $E_k$ corresponding to each second angle.

Figure 6:
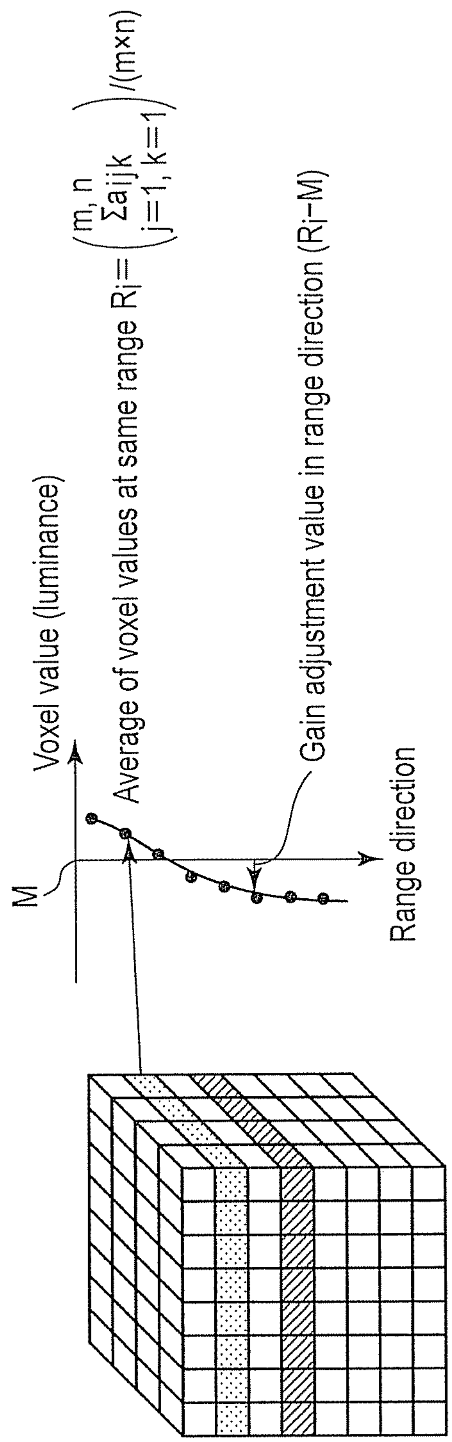
FIG. 6 is a view showing an example of a gain adjustment value in the depth direction according to this embodiment.

FIG. 6 is a view showing an example of a gain adjustment value in the range direction according to this embodiment. The gain adjustment unit 27 calculates the third representative value (the average value of the voxel values at the same range) for each depth (the range direction). More specifically, the gain adjustment unit 27 calculates a third representative value $R_i$ by the following equation:

$$R_i = \left( \sum_{j=1,k=1}^{m,n} a_{ijk} \right) \Big/ (m \times n)$$

The gain adjustment unit 27 then calculates a third gain adjustment value ($R_i$−M) corresponding to each depth by subtracting the average value M from the third representative value $R_i$ corresponding to each depth.

The gain adjustment unit 27 executes three-dimensional gain adjustment for each of a plurality of signal values defined by the first and second angles and depths by using the first to third gain adjustment values. More specifically, the gain adjustment unit 27 executes this operation according to the following equation:

$$b_{ijk}=a_{ijk}-(R_i-M)-(A_j-M)-(E_k-M)$$

where $b_{ijk}$ is a signal value after gain adjustment.

Note that the gain adjustment unit 27 may decide gain adjustment values based on input three-dimensional B-mode data, execute gain adjustment for the three-dimensional B-mode data based on which the gain adjustment values are decided, and execute gain adjustment for each of a plurality of signal values included in the three-dimensional B-mode data input by subsequent scanning. In addition, the gain adjustment unit 27 can decide gain adjustment values based on input three-dimensional B-mode data for each input three-dimensional B-mode data, and execute gain adjustment.

The gradation reversal unit 29 reverses the gradations of the gain-adjusted three-dimensional B-mode data. This reverses the gradations of the parenchyma organ (non-lumen region) from high gradations to low gradations. This also reverses the gradations of the lumen region from low gradations or a transparent state to high gradations. The gradation reversal unit 29 outputs the gradation-reversed three-dimensional B-mode data to the interpolation unit 31 (to be described later). Note that the gradation reversal unit 29 may reverse gradations concerning the signal values of the data output from the threshold processing unit 35 (to be described later).

The interpolation unit 31 executes data interpolation to arrange data on a preset line of sight for rendering processing (to be described later) by using the gradation-reversed three-dimensional B-mode data. The interpolation unit 31 generates line-of-sight data by arranging data on the line of sight (to be described later with reference to FIG. 8) by data interpolation. Note that the interpolation unit 31 may generate line-of-sight data by using the gain-adjusted three-dimensional B-mode data. The interpolation unit 31 outputs the line-of-sight data to the threshold decision unit 33 and threshold processing unit 35 (which will be described later). Note that the interpolation unit 31 may generate volume data (in which voxels are arranged on the lattice elements obtained by dividing a rectangular parallelepiped, which is generally a volume, by a unit length) by converting the raw data generated by the B-mode data generation unit 25 into raw voxels by data interpolation, or may generate line-of-sight data from raw data or volume data.

The threshold decision unit 33 executes statistical processing by using the line-of-sight data. Note that the threshold decision unit 33 may execute statistical processing by using the volume data generated by raw voxel conversion, or may execute statistical processing by using raw data. In general, a prerequisite for the execution of statistical processing is that gain adjustment has been complete, and it does not matter whether gradation reversal processing has been complete. More specifically, the threshold decision unit 33 calculates an average value and a standard deviation based on the magnitudes and frequencies of signal values in line-of-sight data. The threshold decision unit 33 then calculates a threshold by using the average value, a predetermined constant, and the standard deviation as follows:

threshold=average value+predetermined constant×standard deviation

Note that the threshold decision unit 33 may use the magnitudes or the like of pixel values, luminance values, and gradation values instead of the magnitudes of signal values. It is also possible to use other dispersion (variance, average deviation, or the like) instead of a standard deviation. Note that it is possible to use a mode value or median value instead of an average value.

In general, the threshold decision unit 33 calculates a threshold as follows by using a value (to be referred to as the fourth representative value hereinafter) representing line-of-sight data, a dispersion, and a predetermined constant. The fourth average value is, for example, a generic term of the above average value, mode value, median value, and the like.

threshold=fourth representative value+predetermined constant×dispersion

A predetermined constant in the above two equations is set in advance so as to set a threshold between a signal value concerning a lumen region (e.g., a blood vessel or biliary duct) and a signal value concerning a non-lumen region (e.g., a parenchyma organ in the object). In the distribution of signal values concerning a non-lumen region, variations due to an object, a diagnostic region, and the like are empirically small. For this reason, a predetermined constant can be decided by using the data of various objects and diagnostic regions and can be set in advance. The number of set values to be set may be one or a set value may be set for each diagnostic region. In this case, a predetermined constant is stored in a memory (not shown) in advance. The threshold decision unit 33 reads out a predetermined constant from the memory (not shown) and calculates a threshold. Note that the operator can adjust the above predetermined constant via the input unit 14 (to be described later), as needed. Note that the threshold decision unit 33 can decide a threshold based on a line-of-sight data set constituted by line-of-sight data generated for each scan in a scanned region.

The threshold processing unit 35 executes threshold processing for the line-of-sight data by using the threshold decided by the threshold decision unit 33. The threshold processing unit 35 extracts signal values concerning the lumen region from a plurality of signal values included in the line-of-sight data by threshold processing. More specifically, if the line-of-sight data has undergone gradation reversal, the threshold processing unit 35 assigns zeros to a plurality of signal values smaller than the threshold. Note that the threshold processing unit 35 may clip a plurality of signal values larger than the threshold from a plurality of signal values included in the line-of-sight data. In addition, the threshold processing unit 35 may remove a plurality of signal values smaller than the threshold from a plurality of signal values included in the line-of-sight data. The threshold processing unit 35 outputs the line-of-sight data having undergone threshold processing to the image generation unit 37 (to be described later).

When executing the above threshold processing before gradation reversal, the threshold processing unit 35 uses the threshold (to be described later) decided by the threshold decision unit 33 and assigns the maximum value (e.g., 255 in this case) to each of a plurality of signal values larger than the threshold decided by the threshold decision unit 33.

In addition, the threshold processing unit 35 can also extract signal values concerning a non-lumen region by reversing the magnitude relationship in the above threshold processing. Note that the threshold processing unit 35 may be incorporated in the image generation unit 37 (to be described later).

The image generation unit 37 executes rendering processing by using the line-of-sight data output from the threshold processing unit 35. Note that if the data having undergone threshold processing is raw data or volume data, the image generation unit 37 execute rendering processing after the interpolation unit 31 converts the data into line-of-sight data by interpolation processing. If the data having undergone threshold processing is data before gradation reversal, the image generation unit 37 executes rendering processing after the gradation reversal unit 29 performs gradation reversal processing. The image generation unit 37 generates a two-dimensional ultrasonic image concerning the lumen region by rendering processing. Volume rendering as rendering processing will be described below with reference to FIG. 7. Note that rendering processing is not limited to volume rendering, and may be, for example, maximum intensity projection (to be referred to as MIP hereinafter).

Figure 7:
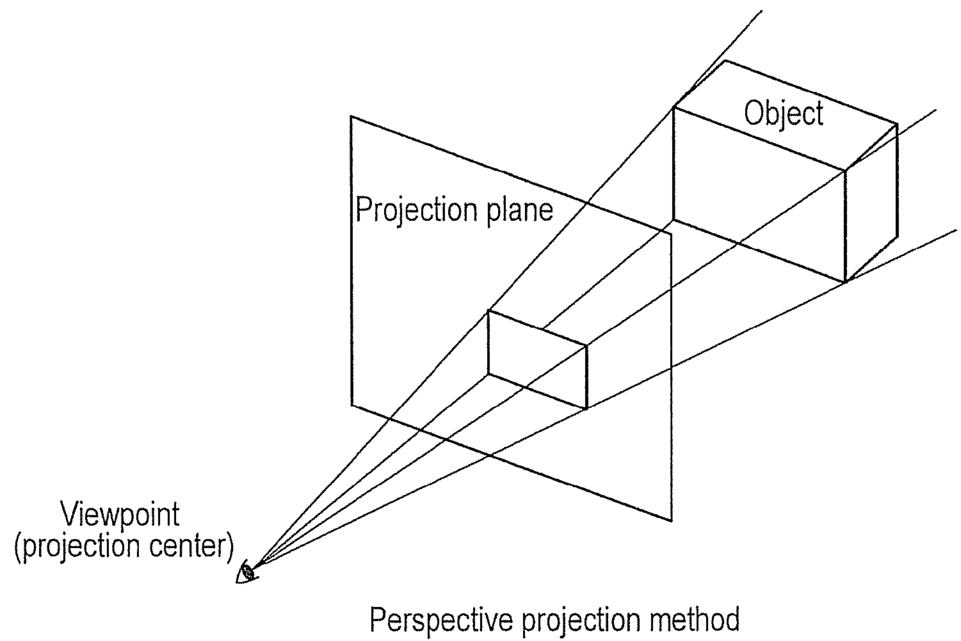
FIG. 7 is a view showing an example of a perspective projection method in rendering processing according to this embodiment.

The image generation unit 37 executes a projection concerning line-of-sight data to display a three-dimensional object on a two-dimensional monitor on the display unit 13 (to be described later) by rendering processing. That is, the image generation unit 37 generates an image on a two-dimensional plane by projecting a three-dimensional object on a projection plane. Projection methods include a perspective projection method and a parallel projection method. FIG. 7 is a view showing an example of the perspective projection method in rendering processing. The perspective projection method is a projection method in which a viewpoint (projection center) is located within a finite length from the object. This method projects a smaller image of the object on a projection plane as the distance from the viewpoint and the object increases (with an increase in distance from the viewpoint). Although not shown, the parallel projection method is a projection method in which the viewpoint is located at an infinite distance from the object. Note that when performing volume rendering, the image generation unit 37 may use either of the projection methods.

Figure 8:
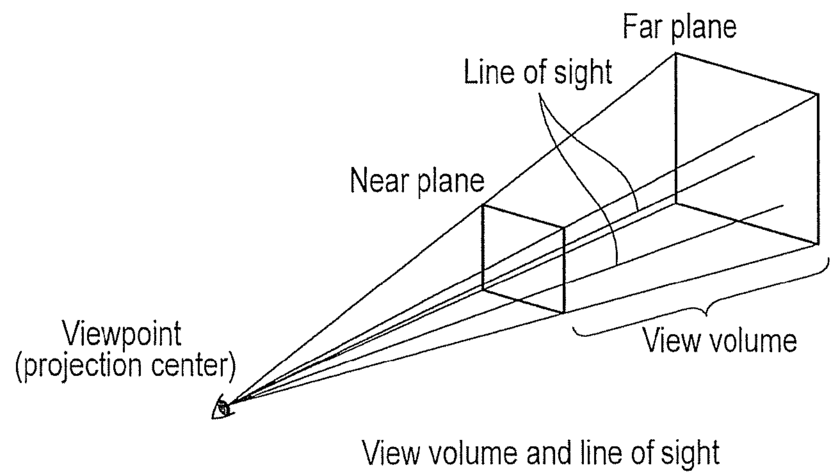
FIG. 8 is a view showing an example of a line of sight and view volume of the perspective projection method in rendering processing according to this embodiment.

FIG. 8 is a view showing an example of a line of sight and view volume concerning the perspective projection method in rendering processing according to this embodiment. A view volume is a region in which the object is viewed from the viewpoint. In this case, the object corresponds to an ROI or part of the ROI in ultrasonic three-dimensional scanning. A plurality of signal values included in the three-dimensional B-mode data obtained by ultrasonic three-dimensional scanning are arranged on lines of sight in a view volume by interpolation processing by the interpolation unit 31 after gradation reversal. A line of sight is a straight line extending from a viewpoint in each direction extending through a view volume. Note that the term "line of sight" complies with the above definition, and differs from the definition of a line of sight in general three-dimensional computer graphics.

The image generation unit 37 projects a plurality of signal values in a view volume arranged on one line of sight on a projection plane by the volume rendering method. With this operation, the image generation unit 37 generates the image data of one pixel of an ultrasonic image. The image generation unit 37 generates an ultrasonic image by executing the above processing for each of a plurality of lines of sight. At this time, the image generation unit 37 converts a signal string in the generated ultrasonic image into a signal string in a general video format typified by a TV format or the like, and generates an ultrasonic diagnostic image as a display image. Note that the image generation unit 37 may generate a color/Doppler image based on the color/Doppler signal output from a color/Doppler processing unit (not shown). The image generation unit 37 may generate a multiplanar reconstruction (to be referred to as MPR hereinafter) image concerning an ROI based on the three-dimensional B-mode data. With regard to an MPR image, the image generation unit 37 generates an MPR image as a two-dimensional ultrasonic image concerning the lumen region by using the three-dimensional B-mode data having undergone the gain adjustment, threshold processing, and gradation reversal processing. In addition, the image generation unit 37 generates an MPR image with uniform sensitivity by using the three-dimensional B-mode data having undergone the gain adjustment.

The storage unit 39 stores a plurality of reception delay patterns with different focus depths, control programs for the ultrasonic diagnostic apparatus 1, a diagnostic protocol, various kinds of data such as transmission/reception conditions, three-dimensional B-mode data, ultrasonic images and MPR images generated by the image generation unit 37, predetermined reference values used by the gain adjustment unit 27, predetermined constants used by the threshold decision unit 33, a program concerning an algorithm for deciding a gain adjustment value, a program concerning an algorithm for deciding a threshold, and the like. The storage unit 39 stores an ultrasonic image, line-of-sight data, and the like immediately before freeze operation performed via the input unit 14.

The control processor 41 reads out transmission/reception conditions and an apparatus control program stored in the storage unit 39 based on mode selection, selection of a reception delay pattern list, and transmission start/end input by the operator via the input unit 14, and controls the apparatus main body 12 in accordance with these pieces of information. For example, the control processor 41 controls the gain adjustment unit 27, the gradation reversal unit 29, the interpolation unit 31, the threshold decision unit 33, and the threshold processing unit 35 in accordance with control programs read out from the storage unit 39.

The interface unit 43 is an interface concerning the input unit 14, a network, an external storage device (not shown), and a biological signal measurement unit (not shown). Data such as ultrasonic images, analysis results, and the like obtained by the apparatus main body 12 can be transferred to other apparatuses via the interface unit 43 and the network.

Figure 9:
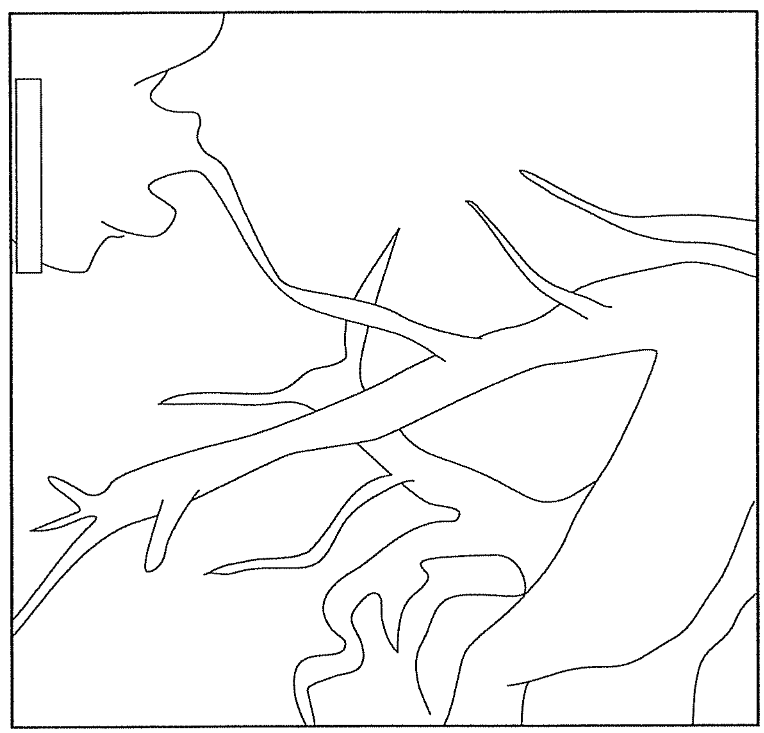
FIG. 9 is a view showing an example of the cavity image obtained by this embodiment.
Figure 17:
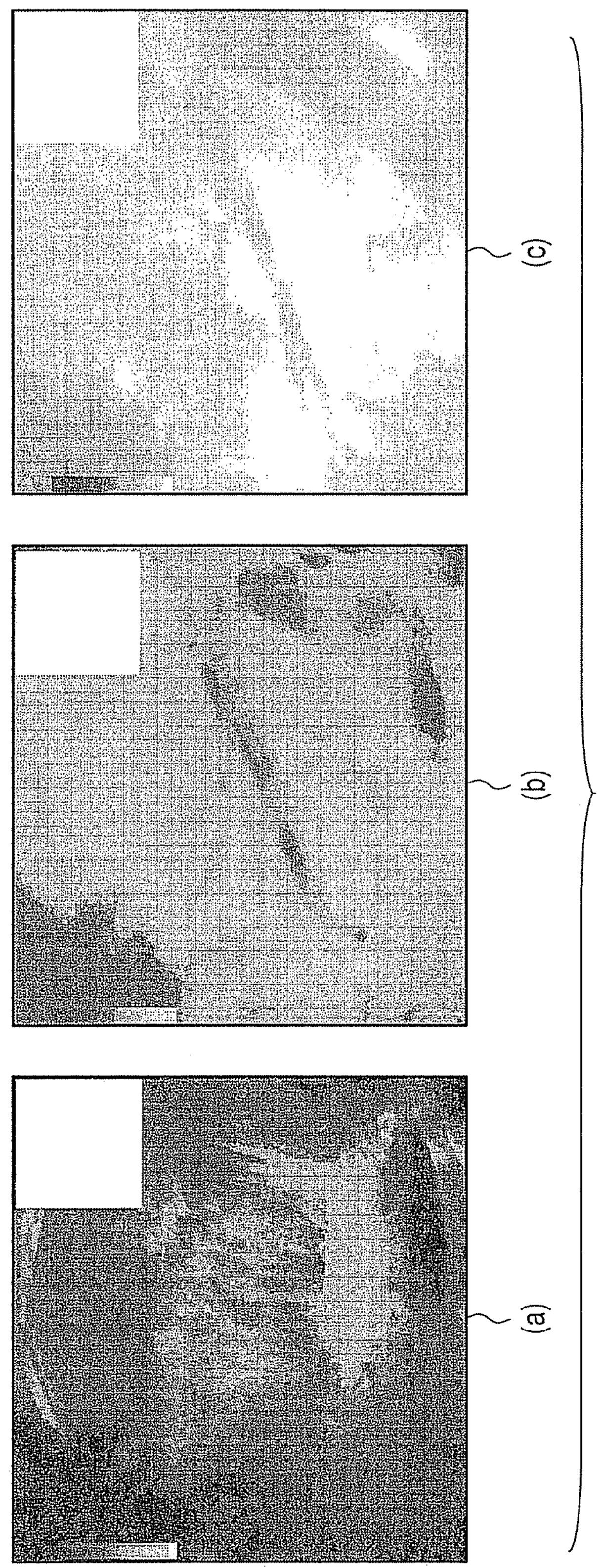
FIG. 17 shows an example of a conventional cavity image.

The display unit 13 displays an ultrasonic image and an MPR image based on outputs from the image generation unit 37. The display unit 13 displays a lumen region (e.g., a blood vessel or biliary duct) in a scanned region (or an ROI) by the above processing. FIG. 9 is a view showing an example of an image (cavity image) displayed by the display unit 13 with high luminance. Note that the display unit 13 may execute adjustments concerning brightness, contrast, dynamic range, γ correction, and the like and color mapping for the ultrasonic image and MPR image generated by the image generation unit 37.

The input unit 14 is connected to the interface unit 43 and inputs various kinds of instruction, commands, information, selections, and settings from the operator to the apparatus main body 12. The input unit 14 includes input devices such as a trackball, switch buttons, mouse, and keyboard (not shown). The input device detects the coordinates of a cursor displayed on the display screen, and outputs the detected coordinates to the CPU 41. Note that the input device may be a touch panel provided to cover the display screen. In this case, the input unit 14 detects a touched and designated coordinates by a coordinate reading principle such as an electromagnetic induction scheme, magnetostriction scheme, or a pressure-sensitive scheme, and outputs the detected coordinates to the CPU 41. When, for example, the operator operates the end button or freeze button of the input device 14, the transmission/reception of ultrasonic waves is terminated, and the apparatus main body 12 is set in a pause state. Note that the input unit 14 may input a predetermined reference value to the apparatus main body 12 in accordance with an instruction from the operator. The input unit 14 may also input a predetermined constant used by the threshold decision unit 33.

(Cavity Image Generation Function)

The cavity image generation function is a function of generating an ultrasonic image (to be referred to as a cavity image hereinafter) by executing gain adjustment based on three-dimensional B-mode data, deciding a threshold based on the gain-adjusted three-dimensional B-mode data, and executing threshold processing based on the decided threshold. Processing concerning the cavity image generation function (to be referred to as cavity image generation processing hereinafter) will be described below.

FIG. 10 is a flowchart showing a procedure for the processing of generating a cavity image.

Before ultrasonic transmission/reception with respect to an object, the apparatus executes input of patient information, setting and updating of transmission/reception conditions and various kinds of ultrasonic data acquisition conditions, and the like in accordance with instructions from the operator via the input unit 14. The storage unit 39 stores these settings and updates. Upon completion of these input, selection, and setting operations, the operator brings the ultrasonic probe 11 into contact with the body surface of the object at a predetermined position. The transmission/reception unit 23 then supplies ultrasonic waves to the object. A received signal is generated based on the reception of an echo signal (i.e., ultrasonic scanning) corresponding to the transmitted ultrasonic waves (step Sa1).

The apparatus generates a three-dimensional B-mode data based on the generated received signal (step Sa2). FIG. 11 shows histograms concerning a plurality of signal values included in the three-dimensional B-mode data before gain adjustment. A signal value concerning a parenchyma organ is characterized by being larger than a signal value concerning a lumen region. Histograms of signal values concerning artifacts exist so as to overlap the histogram of the signal value concerning the lumen region.

The apparatus decides gain adjustment values for each range depth and each of the first and second angles based on the three-dimensional B-mode data (step Sa3). The apparatus executes three-dimensional gain adjustment for each of a plurality of signal values included in the three-dimensional B-mode data by using the decided gain adjustment values (step Sa4). Performing gain adjustment will make the histogram concerning the parenchyma organ contain the histograms concerning the artifacts. This discriminates the histogram concerning the lumen region from the histogram concerning the parenchyma organ.

The logic of discriminating a histogram concerning a lumen region and a histogram concerning an artifact by three-dimensional gain adjustment will be described below. The parenchyma organ spreads throughout a wide region as compared with the lumen region in a space in a scanned region. On the other hand, the lumen region is narrow and localized as compared with the parenchyma organ, and hence occupies a smaller volume in the scanned region (l×m×n) than the parenchyma organ. In addition, the areas occupied by the lumen region in an area (l×n) corresponding to the azimuth direction, area (l×m) corresponding to the elevation direction, and area (m×n) corresponding to the range direction are smaller than those occupied by the parenchyma organ. Therefore, the predetermined reference value and the first to third representative values become values reflecting the parenchyma organ. In contrast, the artifacts originate from the echo signal of the parenchyma organ, and hence spread throughout a wide region as compared with the lumen region in the space in the scanned region like the parenchyma organ. In consideration of them, the predetermined reference value and the first to third representative values become values reflecting the parenchyma organ and artifacts.

For the above reasons, the influence of gain adjustment for the signal values concerning the parenchyma organ and artifacts is larger than the influence of gain adjustment for the signal value concerning the lumen region. That is, the apparatus executes gain adjustment for only the artifacts more strongly near the signal values at which the histogram concerning the lumen region and the histograms concerning the artifacts overlap each other. In this case, although the histograms concerning the lumen region and artifacts overlap each other, they are spatially separate. This makes it necessary to perform such gain adjustment. This gain adjustment discriminates the histogram concerning the lumen region from the histograms concerning the artifacts. FIG. 12 is a view showing an example of histograms concerning the magnitudes of a plurality of signal values included in three-dimensional B-mode data after gain adjustment.

The gradation reversal unit 29 reverses the gradations of the plurality of signal values for which gain adjustment has been executed. FIG. 13 is a view showing an example of a graph concerning gradation reversal. According to this graph, if, for example, an input signal value is 10 and the maximum value of the signal value is 255, the signal value to be output is 255−10=245. The apparatus executes statistical processing by using a plurality of gradation-reversed signal values (step Sa5). With the statistical processing in step Sa5, the apparatus calculates, for example, the average value and standard deviation of the signal values of the overall histogram. In the scanned region and ROI, the volume of the parenchyma organ is larger than that of the lumen region. For this reason, the average value and standard deviation of the signal values of the overall histogram are close to those of the signal values of the histogram of the parenchyma organ. The apparatus decides a threshold by using the average value and standard deviation calculated by statistical processing (step Sa6). The apparatus executes threshold processing for the three-dimensional B-mode data for which gain adjustment has been executed (step Sa7). FIG. 14 is a view showing histograms of a plurality of signal values included in three-dimensional B-mode data having undergone gain adjustment and gradation reversal, together with a decided threshold. The threshold in FIG. 14 is, for example, the value obtained by adding an average value to a predetermined constant multiple of a standard deviation. Performing threshold processing will remove the histograms concerning the parenchyma organ and the artifacts. The apparatus generates an ultrasonic image concerning the lumen region based on the three-dimensional B-mode data having undergone threshold processing (step Sa8).

Note that the apparatus may execute gain adjustment, gradation reversal, and threshold processing for each of raw data, volume data, and line-of-sight data. Alternatively, the apparatus may partly execute gain adjustment, gradation reversal, and threshold processing for each of raw data, volume data, and line-of-sight data. In addition, it is possible to reverse the order of execution of gain adjustment and gradation reversal. It is also possible to reverse the order of execution of gradation reversal and threshold processing. When executing threshold processing before gradation reversal, the apparatus decides a threshold by the following calculation:

threshold=average value−predetermined constant×standard deviation

In general, threshold=fourth representative value−predetermined constant×dispersion degree Since the histogram concerning the lumen region exists less than the threshold and the histogram concerning the parenchyma organ exist equal to or more than the threshold, the apparatus removes the histogram equal to or more than the threshold. That is, the apparatus assigns the maximum gradation value (e.g., 255) to each of a plurality of signal values belonging to the histogram equal to or more than the threshold. FIG. 15 is a view showing histograms of a plurality of signal values included in three-dimensional B-mode data after gain adjustment, together with a threshold, when a histogram concerning the parenchyma organ is removed before gradation reversal.

(Gain Adjustment Value Decision Function)

The gain adjustment value decision function is a function of deciding a gain adjustment value for each of the first angle defining a scan range in the depth direction and the azimuth direction on each scanning line in a scanned region and the second angle defining a scan range in the elevation direction in the scan region based on three-dimensional B-mode data. Processing concerning the gain adjustment value decision function (to be referred to as gain adjustment value decision processing hereinafter) will be described below.

FIG. 16 is a flowchart showing a procedure for the processing of deciding a gain adjustment value according to step Sa3 in FIG. 10. The apparatus calculates the average value (to be referred to as the reference value hereinafter) of a plurality of signal values included in three-dimensional B-mode data (step Sb1). The apparatus calculates, for each of a plurality of first angles, the average value (to be referred to as the first average value hereinafter) of a plurality of signal values with the same first angle (step Sb2). The apparatus calculates, for each first angle, the first difference (first gain adjustment value) obtained by subtracting the reference value from the first average value (step Sb3). The apparatus calculates, for each of a plurality of second angles, the average value (to be referred to as the second average value hereinafter) of a plurality of signal values with the same second angle (step Sb4). The apparatus calculates, for each second angle, the second difference (second gain adjustment value) obtained by subtracting the reference value from the second average value (step Sb5). The apparatus calculates, for each of a plurality of depths in a scanned region, the average value (to be referred to as the third average value hereinafter) of a plurality of signal values with the same depth (step Sb6). The apparatus calculates, for each depth, the third difference (third gain adjustment value) by subtracting the reference value from the third average value (step Sb7). Note that it is possible to change the order of calculation of the first to third gain adjustment values, as needed. The first to third differences are decided as the first to third gain adjustment values respectively associated with the first angle, second angle, and depth in each of a plurality of signal values (step Sb8). Performing such gain adjustment makes the signal values, pixel values, or gradations concerning the parenchyma organ approach uniformity.

According to the above arrangement, the following effects can be obtained.

The ultrasonic diagnostic apparatus 1 can execute three-dimensional gain adjustment for each of a plurality of signal values included in three-dimensional B-mode data by using three-dimensional gain adjustment values decided based on the three-dimensional B-mode data. Executing statistical processing by using a plurality of signal values included in the gain-adjusted three-dimensional B-mode data or volume data can decide a threshold used for discriminating a lumen region and a non-lumen region. Executing threshold processing by using the decided threshold can generate an image (cavity image) concerning the lumen region. These make it possible to generate an ultrasonic image concerning the lumen region with greatly reduced artifacts, thus improving the diagnostic performance. In addition, since the operability for obtaining a cavity image improves, the examination efficiency improves.

In addition, the ultrasonic diagnostic apparatus 1 can improve the real-time performance because the algorithm for deciding gain adjustment values uses simple averages instead of using a complicated algorithm for performing processing while discriminating a parenchyma organ and a lumen region. This makes it possible to further update gain adjustment values every time three-dimensional B-mode data is generated, and to execute optimal gain adjustment. In addition, since the apparatus decides gain adjustment values for each of a plurality of signal values included in three-dimensional B-mode data, it is possible to execute accurate gain adjustment. For these reasons, it is possible to achieve improvements in real-time performance and detection performance of a lumen region. This improves the examination efficiency.

In addition, the ultrasonic diagnostic apparatus 1 can perform gain adjustment and threshold processing for even three-dimensional B-mode data obtained by one scan on a scanned region as in the single sweep mode. Furthermore, this embodiment is not limited to the single sweep mode, and it is also possible to execute gain adjustment and threshold processing in a case in which real-time scanning is performed and a case in which an ultrasonic image is generated by performing freeze operation during real-time scanning.

Furthermore, according to the ultrasonic diagnostic apparatus 1, for example, even if STC (Sensitivity Time Control) gain adjustment and B-mode gain adjustment are performed to adjust the luminance of a B-mode image, an optimal threshold is maintained, and the operability greatly improves. The following is the reason for this. In B-mode gain adjustment, since the distribution state of a histogram remains the same and the signal values, gradations, and the like in the overall distribution shift, it is not necessary to re-set a predetermined constant. In addition, in STC gain adjustment, although signal values or gradations at a given depth change. However, the gain adjustment value decision function in this embodiment decides gain adjustment values so as to make the signal values concerning a parenchyma organ approach uniformity. This eliminates the necessity to re-set a predetermined constant.

In addition, the ultrasonic diagnostic apparatus 1 can execute three-dimensional gain adjustment. For example, this improves the accuracy of a lumen region in the flythrough mode and the like. This improves the diagnostic efficiency.

In addition, when the technical idea of the ultrasonic diagnostic apparatus 1 is to be implemented by a medical image processing apparatus as a modification of the above embodiment, for example, the apparatus includes the constituent elements in the solid line in the block diagram of FIG. 1. At this time, the processing concerning the generation of a cavity image corresponds to the processing from step Sa3 to step Sa8. These processes are the same as in the embodiment. Note that three-dimensional B-mode data in step Sa3 is stored in the storage unit 39 in advance. In addition, the medical image processing apparatus can also execute the above processing by reading a DICOM file (e.g., three-dimensional B-mode data) output from the ultrasonic diagnostic apparatus. Furthermore, each function according to the embodiment can be implemented by installing programs for executing the processing in a computer such as a workstation and expanding them in the memory. In this case, the programs which can cause the computer to execute the corresponding techniques can be distributed by being stored in storage media such as magnetic disks (Floppy® disks, hard disks, and the like), optical disks (CD-ROMs, DVDs, and the like), and semiconductor memories.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
- an ultrasonic probe configured to include a plurality of ultrasonic transducers;
- a transmission/reception unit configured to supply a driving signal to each of the ultrasonic transducers and generate a received signal corresponding to a scanned region based on each reception echo signal generated by each of the ultrasonic transducers;
- a B-mode data generation unit configured to generate three-dimensional B-mode data based on the received signal;
- a gain adjustment unit configured to execute gain adjustment for the three-dimensional B-mode data by using gain adjustment values respectively decided for a depth on each scanning line, an azimuth direction and an elevation direction in the scanned region;
- a threshold decision unit configured to decide a threshold used for discriminating a lumen region and a non-lumen region in the scanned region by using the three-dimensional B-mode data for which the gain adjustment has been executed;
- a threshold processing unit configured to execute threshold processing to discriminate data concerning the non-lumen region from the three-dimensional B-mode data for which the gain adjustment has been executed, by using the decided threshold; and
- an image generation unit configured to generate an ultrasonic image concerning the lumen region based on the three-dimensional B-mode data for which the threshold processing has been executed.

2. The apparatus of claim 1, wherein the gain adjustment unit is configured to decide, as the gain adjustment values,
- a first difference between a predetermined reference value and a first representative value representing the three-dimensional B-mode data with a same angle in the azimuth direction,
- a second difference between the reference value and a second representative value representing the three-dimensional B-mode data with a same angle in the elevation direction, and
- a third difference between the reference value and a third representative value representing the three-dimensional B-mode data with a same depth.

3. The apparatus of claim 1, wherein the gain adjustment unit is configured to execute gain adjustment for three-dimensional B-mode data generated at a different time from the three-dimensional B-mode data used to decide the gain adjustment values.

4. The apparatus of claim 1, further comprising:
- a display unit configured to display the ultrasonic image; and
- an input unit configured to input operation of freezing the displayed ultrasonic image,
- wherein the gain adjustment unit is configured to execute gain adjustment for three-dimensional B-mode data concerning the frozen ultrasonic image by using the gain adjustment values decided based on the three-dimensional B-mode data concerning the frozen ultrasonic image in response to the freezing operation input via the input unit.

5. The apparatus of claim 1, wherein the threshold decision unit is configured to decide, as the threshold, a value obtained by adding a constant multiple of a dispersion degree in a histogram of the three-dimensional B-mode data for which the gain adjustment has been executed to a representative value in the histogram.

6. The apparatus of claim 5, further comprising:
- an input unit configured to input a numerical value indicting the constant multiple.

7. The apparatus of claim 1, wherein the threshold decision unit is configured to decide, as the threshold, a value obtained by subtracting a constant multiple of a dispersion degree in a histogram of the three-dimensional B-mode data for which the gain adjustment has been executed from a representative value in the histogram.

8. The apparatus of claim 1, wherein the image generation unit is configured to generate at least one of a rendering image and a multiplanar reconstruction image as the ultrasonic image concerning the lumen region.

9. An ultrasonic diagnostic apparatus comprising:
- an ultrasonic probe configured to include a plurality of ultrasonic transducers;
- a transmission/reception unit configured to supply a driving signal to each of the ultrasonic transducers and generate a received signal corresponding to a scanned region based on each reception echo signal generated by each of the ultrasonic transducers;
- a B-mode data generation unit configured to generate three-dimensional B-mode data based on the received signal; and a gain adjustment unit configured to execute gain adjustment for the three-dimensional B-mode data by using gain adjustment values respectively decided for a depth on each scanning line, an azimuth direction and an elevation direction in the scanned region, wherein the gain adjustment unit is configured to decide, as the gain adjustment values, a first difference between a predetermined reference value and a first representative value representing the three-dimensional B-mode data with a same angle in the azimuth direction, a second difference between the reference value and a second representative value representing the three-dimensional B-mode data with a same angle in the elevation direction, and a third difference between the reference value and a third representative value representing the three-dimensional B-mode data with a same depth.

10. The apparatus of claim 9, further comprising:

an image generation unit configured to generate an ultrasonic image, wherein the image generation unit is configured to generate a multiplanar reconstruction image based on the three-dimensional B-mode data for which the gain adjustment has been executed.

11. A medical image processing apparatus comprising:

a storage unit configured to store three-dimensional B-mode data;

a gain adjustment unit configured to execute gain adjustment for the three-dimensional B-mode data by using gain adjustment values respectively decided for a depth on each scanning line, an azimuth direction and an elevation direction in a scanned region based on the three-dimensional B-mode data;

a threshold decision unit configured to decide a threshold used for discriminating a lumen region and a non-lumen region in the scanned region by using the three-dimensional B-mode data for which the gain adjustment has been executed;

a threshold processing unit configured to execute threshold processing to discriminate data concerning the non-lumen region from the three-dimensional B-mode data for which the gain adjustment has been executed, by using the decided threshold; and an image generation unit configured to generate an ultrasonic image concerning the lumen region based on the three-dimensional B-mode data for which the threshold processing has been executed.

* * * * *